US00PP18807P2

(12) United States Plant Patent
Gravois et al.

(10) Patent No.: US PP18,807 P2
(45) Date of Patent: May 13, 2008

(54) SUGAR CANE VARIETY NAMED 'L99-226'

(50) Latin Name: ***Saccharum* sp.**
Varietal Denomination: L99-226

(75) Inventors: Kenneth A. Gravois, Baton Rouge, LA (US); Keith P. Bischoff, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 1 day.

(21) Appl. No.: 11/599,678

(22) Filed: Nov. 15, 2006

(51) Int. Cl.
*A01H 5/00* (2006.01)

(52) U.S. Cl. ..... Plt./258
(58) Field of Classification Search ..... Plt./258
See application file for complete search history.

(56) References Cited

U.S. PATENT DOCUMENTS

PP10,839 P 3/1999 Holder
PP12,710 P2 6/2002 Holder
2006/0150291 P1 7/2006 Gravois

OTHER PUBLICATIONS

Bischoff, K.P. et al., "The Development of New Sugarcane Varieties at the LSU AgCenter," J. Amer. Soc. Sugar Technol., vol. 24, pp. 142–164 (2004).

Legendre, B.L. et al., "Registration of 'HoCP85–845' Sugarcane," Crop Sci., vol. 34, p. 820 (1994).

Legendre, B.L. et al., "Registration of 'HoCP91–555' Sugarcane," Crop Sci., vol. 40, p. 1506 (2000).

Legendre, B.L. et al., "the 2003 Louisiana Sugarcane Variety Survey," Sugar Bulletin, vol. 82(9), pp. 22–28 (2004).

Milligan, S.B. et al., "Registration of 'LCP85–384' Sugarcane," Crop Sci., vol. 34, pp. 819–820 (1994).

Tew, T.L. et al., "Registration of 'HoCP96–540' Sugarcane," Crop Sci., vol. 44, pp. 785–786 (2005).

*Primary Examiner*—Wendy C. Haas
(74) *Attorney, Agent, or Firm*—John H. Runnels; Bonnie J. Davis; James C. Carver

(57) ABSTRACT

A new variety of sugarcane, identified as 'L99-226', is disclosed having superior sugarcane rust disease resistance, and high sugar/sucrose content and cane yield characteristics.

5 Drawing Sheets

Genus and species name: *Saccharum* sp.
Variety denomination: 'L99-226'.

This invention pertains to a new and distinct variety of sugarcane.

BACKGROUND OF THE INVENTION

Sugarcane variety, *Saccharum* sp., is a giant, thick, perennial grass of the Gramineae family cultivated in tropical, subtropical, and some temperate regions worldwide for its sweet sap, which is a major source of sugar and molasses. Sugarcane is believed to have originated in what is now known as New Guinea.

SUMMARY OF THE INVENTION

Genus and Species Name

This new and distinct sugarcane variety, *Saccharum* sp., demonstrates superior sugarcane rust disease resistance, early and high sugar/sucrose content, and cane yield characteristics as compared to other available sugarcane varieties known to the inventors. A new variety of sugarcane identified as 'L99-226' is disclosed having high cane yield, early maturity, high sucrose content, resistance to sugarcane rust disease, and good ratooning ability.

Variety Denomination

This new and distinct sugarcane variety is identified as 'L99-226', and is characterized by its purplish green stalk color.

BRIEF DESCRIPTION OF THE DRAWINGS

The file of this patent contains at least one photograph executed in color. Copies of this patent or patent application publication with color drawing(s) will be provided by the Office upon request and payment of the necessary fee.

DETAILED BOTANICAL DESCRIPTION

This new variety of sugarcane, identified as 'L99-226', originated as a true seedling, produced by a biparental cross (identified by the inventors as 'XL94-128' (unpatented)) between the female parent 'HoCP89-846' (unpatented) and the male parent 'LCP81-30' (unpatented). In this form of variety designation, which is well known among sugarcane breeders, the "L" indicates the cross and selection occurred in the sugarcane breeding program in St. Gabriel, La. The "99" indicates the year of assignment of a permanent variety identification, and "226" is a unique number assigned to varieties that year. The cross was made in 1994 in St. Gabriel, La., and this new variety was selected from among the progeny of the cross. Early stage selection among the progeny was done between the years 1994 and 1998. The seedling of 'L99-226' was germinated from a "true seed" in January, 1995 and transplanted to the field in April, 1995. Selection occurred in the first ratoon crop in 1996 from a single stool of sugarcane. Two stalks were cut and transplanted successfully for asexual reproduction. Asexual propagation of the new cultivar by cuttings has shown that the unique features of this new sugarcane are stable, and the plant reproduces true to type in successive generations of asexual propagation. Plants described herein were characterized on Sep. 11-19, 2006, at approximately 160-175 days in age from spring emergence. The stalks characterized were from inner rows unexposed to direct sunlight. See K. P. Bischoff, et al., "The Development of New Sugarcane Varieties at the LSU AgCenter," *J. Amer. Soc. Sugar Technol.,* vol 24, pp. 142-164 (2004).

Neither 'HoCP89-846' nor 'LCP81-30' ever attained commercial status, but both have been used as parents in the sugarcane breeding program in St. Gabriel, La. The male parent, 'LCP81-30', exhibits average cane yield, very early maturity, and high sucrose content. The female parent, 'HoCP89-846', exhibits high cane yield and average sucrose content characteristics, but was not considered for commercial production due to high fiber content (14.0%) and extreme susceptibility to leaf scald disease. 'L99-226' was developed to provide a new variety with similar maturity, higher sucrose content and cane yield, and improved sugarcane rust resistance.

'L99-226' is characterized by darker green stalks with purplish hues. Color terminology used herein is in accordance with the MUNSELL® color charts for plant tissue and the MUNSELL® Book of Color for stalk and leaf determination (Munsell Color, Gretag Macbeth LLC, New Windsor, N.Y.). The color descriptions and color illustrations are as nearly true as is reasonably possible. However, it is understood that both color and other phenotypic expressions described herein may vary from plant to plant with differences in growth, environment and cultural conditions, without any change in the genotype of the variety 'L99-226'.

Figure 1:
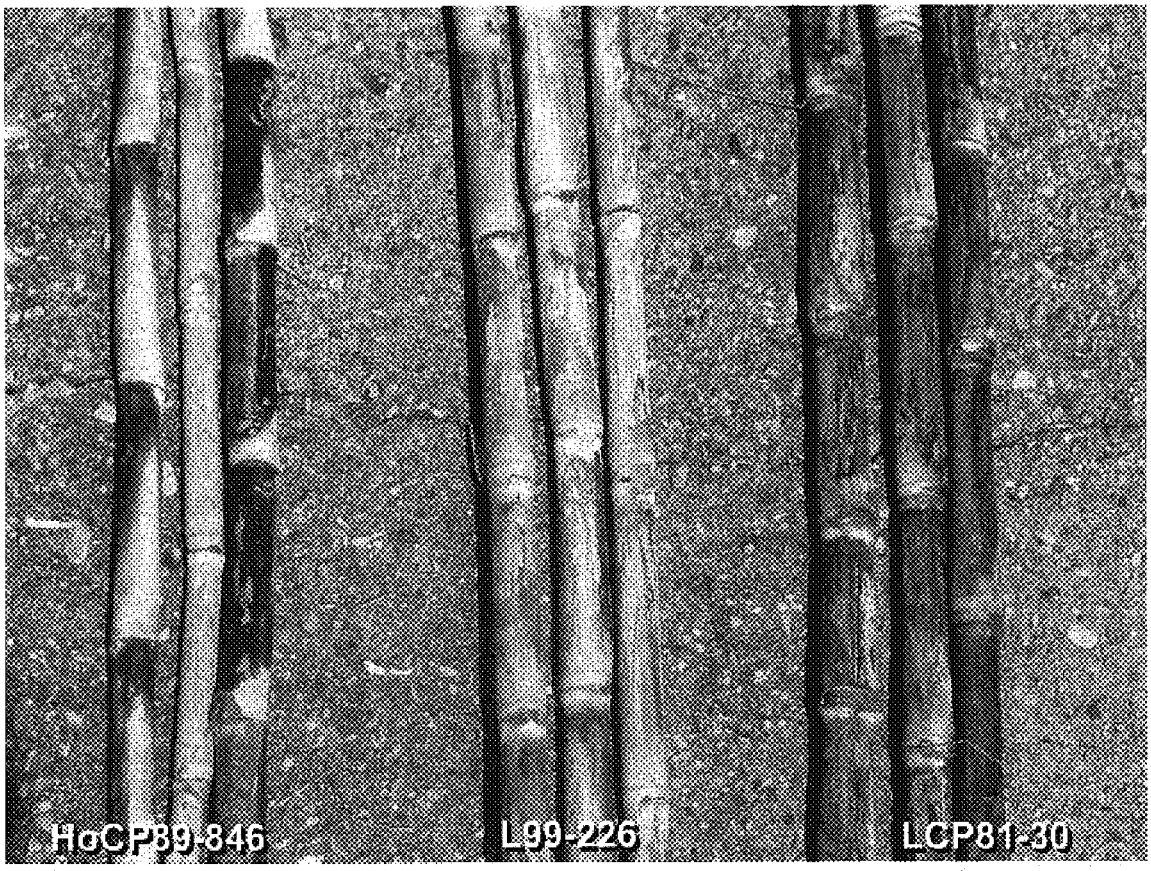
FIG. 1 is a color photograph of the stalk of the novel variety of sugarcane identified as 'L99-226' and other sugarcane varieties identified as 'HoCP89-846' and 'LCP81-30', which were used for comparison tests.

FIG. 1 depicts stalks of 'L99-226', its female parent 'HoCP89-846', and male parent 'LCP81-30'. An extensive white wax bloom covers the stalk of 'L99-226', which is more abundant than the wax blooms of 'HoCP89-846' and 'LCP81-30'. The wax color (BG-PB 9/10PB) is similar for all three varieties. The stalk color of each variety varies under a wax bloom (unexposed to sunlight). 'L99-226' exhibits darker green stalks with purple hues [10 Y (yellow) 6/6] as compared to that of 'HoCP89-846', which is greenish yellow [5 GY (yellow) 5/8], and 'LCP81-30', which exhibits a predominantly purple stalk [2.5R (Red) 2/4]. (The stalk color of each variety became more red or purple when exposed to sunlight.) Colorimetric evaluations using the aforementioned color charts of the stalk, wax, and leaf for 'L99-226', 'HoCP89-846', and 'L99-226' at harvest are shown in Table 1.

'L99-226' exhibited an average mature stalk height (ground level to the top visible dewlap) of 289 cm, as compared to mature stalk heights of 'HoCP89-847' of 282 cm and 'LCP81-30' of 268 cm. The average stalk diameter of 'L99-226' was 25.3 mm, as compared to stalk diameters of 'HoCP89-846' (22.3 mm dia) and 'LCP81-30' (25.2 mm dia). Each variety exhibited conoidal-shaped internodes (fourth internode from ground level) and glabrous (lacking hair) growth rings. Growth ring widths for 'L99-226', 'HoCP89-846', and 'LCP81-30' were 3.85 mm, 2.13 mm, and 2.05 mm, respectively. Root bands of each variety were glabrous with straight sides and exhibited unequally distributed rows of irregularly-shaped root primordia, having diameters between about 0.25 and about 0.50 mm. Root band ring widths for 'L99-226', 'HoCP89-846', and 'LCP81-30' were 4.69 mm, 7.98 mm, and 6.58 mm, respectively. Root bands of 'L99-226' and 'LCP81-30' exhibited a wax layer, while 'HoCP89-846' exhibited a moderate wax layer. Internodes of 'L99-226' were smooth and glabrous with few, if any, corky patches or cracks, and exhibited an average length at the mid-culm of 14.8 cm. Internodes of 'L99-226', 'HoCP89-846', and 'LCP81-30' did not exhibit bud furrows. Buds of each variety were located just above the leaf scar, and were raised above the surface of the root band. 'L99-226' exhibited a narrow ovate bud shape (at the fourth node) with a central germ pore, whereas 'HoCP89-846' exhibited tall deltoids and 'LCP81-30' exhibited round ovate bud shapes. Bud diameters of both 'L99-226' and 'LCP81-30' were just over 6 mm, which was smaller than bud diameters of 'HoCP89-846'. Buds of 'L99-226' were yellow [7.5Y (Yellow) 6/10] without any wax on the surface. None of the three varieties exhibited setaceous or pilose hairs on the buds. See Table 1.

Figure 2:
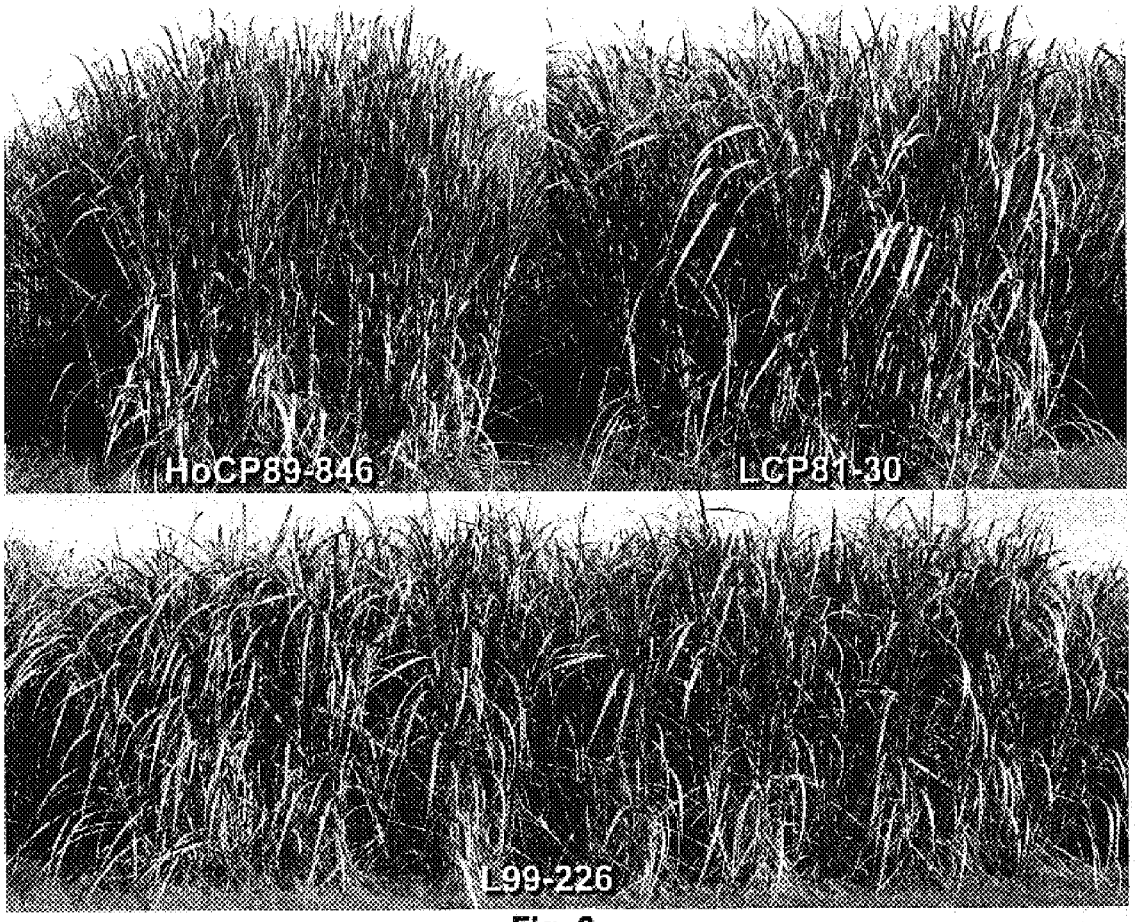
FIG. 2 is a color photograph of the canopy biomass of the novel variety of sugarcane identified as 'L99-226' and other sugarcane varieties identified as 'HoCP89-846' and 'LCP81-30', which were used for comparison tests.

FIG. 2 depicts the canopy biomass of the novel variety of sugarcane identified as 'L99-226' and other sugarcane varieties, identified as 'HoCP89-846' and 'LCP81-30', which were used for comparison tests. The canopies of 'L99-226' and 'LCP81-30' are drooping, whereas the canopy of 'HoCP89-846' is slightly drooping.

Figure 3:
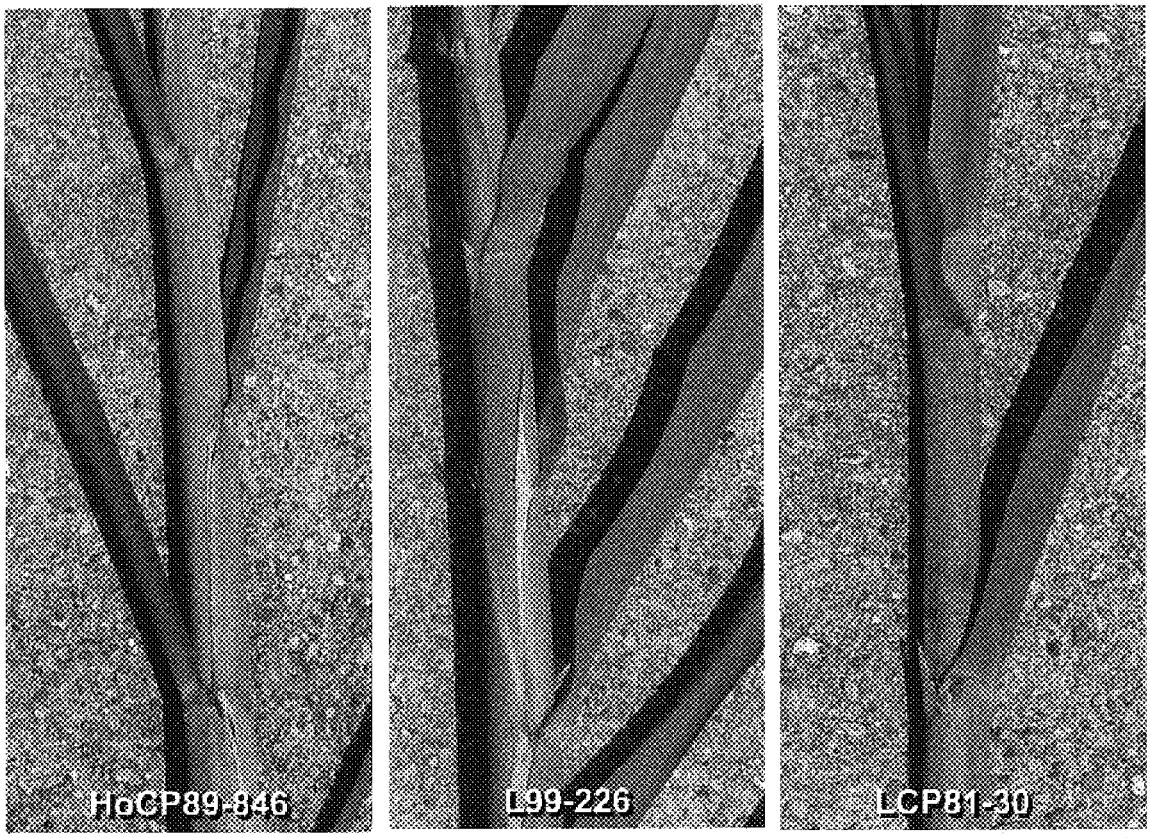
FIG. 3 is a color photograph of the leaf sheath, dewlaps (leaf collars), and auricles of the novel variety of sugarcane identified as 'L99-226' and other sugarcane varieties identified as 'HoCP89-846' and 'LCP81-30', which were used for comparison tests.

FIG. 3 depicts the upper leaf sheaths, dewlaps (leaf collars), and auricles of 'HoCP89-846', 'L99-226', and 'LCP81-30'. The average leaf blade length and width of 'L99-226', 'HoCP89-846', and 'LCP81-30', at the third leaf below the top most visible dewlap, were 178 cm and 4.26 cm, 148 cm and 4.10 cm, and 169 cm and 3.99 cm, respectively. 'L99-226' and 'LCP81-30' exhibited similar green leaf blades [5 GY (Green) Y (Yellow) 4/6] at the second visible dewlap, while 'HoCP89-846' exhibited a slightly different green color [5 G (Green) Y (Yellow) 4/4] at the second visible dewlap.

Each of these varieties exhibited acuminate leaf blades. 'L99-226', 'HoCP89-846', and 'LCP81-10' all exhibited 4-8 mm wide mid-ribs distinctly raised on their abaxial side. The mid-rib color on the abaxial side of the leaf of the three varieties was similar to color of the leaf blade. On the adaxial side, the mid-rib of 'L99-226' had a smooth to concave surface and a whitish color [8.5Y (Yellow) 8.5/2], which was lighter than its leaf blade. Both the leaf blade and mid-rib of 'L99-226' were linear, glabrous with a smooth surface, and relatively thin.

The dewlaps of 'L99-226', HoCP89-846, and 'LCP81-30' were ascending approximately square, deltoid, and flaring ligulate, respectively. Dewlap colors for 'L99-226' and 'HoCP89-846' (a brownish color [10Y (Yellow) 4/6]) were similar. The dewlap color for 'LCP81-30' was [10Y (Yellow) 5/6]. 'L99-226' exhibited a slight, necrotic leaf sheath margin.

The auricle of 'L99-226' was necrotic. The average auricle shape for 'L99-226' was long lanceolate; the average auricle shape for 'HoCP89-846' was short lanceolate; the average auricle shape for 'LCP81-30' was falcate. Auricles were measured on the fourth leaf from the top most visible dewlap.

All three varieties exhibited a broad crescent-shaped ligule. 'L99-226' exhibits a tan color ligule [10YR (Yellow Red) 3/2] having a length of 3.97 mm and a width of 19.28 mm. The ligule region of 'L99-226' exhibited slight pubescence, while 'HoCP89-846' exhibited no pubescence and 'LCP81-30' exhibited moderate pubescence. See Table 1.

TABLE 1

| Trait | Variety L99-226 | Female HoCP89-846 | Male LCP81-30 |
|---|---|---|---|
| Stalk Height (cm) Avg. 10 stalks | 289 | 282 | 268 |
| Stalk Culm Diameter (mm) Avg. 10 stalks | 25.3 | 22.3 | 25.2 |
| Leaf Shape | Drooping | Slightly Drooping | Drooping |
| Leaf Length (cm) Avg. 10 leaves | 178 | 148 | 169 |
| Leaf Width (cm) Avg. 10 leaves | 4.26 | 4.10 | 3.99 |
| Flesh Color | 7.5Y 8/4 | 7.5y 9/2 | 7.5y 9/4 |
| Leaf Color | 5GY-4/6 | 5GY-4/4 | 5GY-4/6 |
| Wax Color | BG-PB 9/10PB | BG-PB 9/10PB | BG-PB 9/10PB |
| Stalk Color | 10Y 6/6 | 5GY 5/8 | 2.5R 2/4 |
| Stalk Buds/Shape(4th node) | Narrow Ovate | Tall Deltoid | Round |
| Auricle Shape | Long Lanceolate | Short Lanceolate | Falcate |
| Auricle Length (mm) Avg. 10 | 35.21 | 7.45 | 31.39 |
| INTERNODE: | | | |
| Waxiness | Extensive | Moderate | Moderate |
| Bud Furrow | None | None | None |
| Growth Ring Width | 3.85 mm | 2.13 mm | 2.05 mm |
| Growth Ring Surface | Rough | Glabrous | Glabrous |
| Root Band Width | 4.69 mm | 7.98 mm | 6.58 mm |
| Stalk Shape | Conoidal | Conoidal | Conoidal |
| 4th Internode from ground level | | | |
| Internode length (cm) Avg. 10 | 14.8 | 13.0 | 15.2 |
| Ligule Shape | Broad Crescent | Broad Crescent | Broad Crescent |
| Leaf Sheath: | | | |
| Average Length (cm) Avg. 10 | 38.17 | 33.67 | 31.83 |
| Color | 5GY 5/4 | 5GY 5/8 | 2.5GY 5/6 |
| Leaf Scar Shape | Obliquely | Horizontal | Horizontal |
| Bud: | | | |
| Bud Diameter (mm) Avg 10 | 6.78 | 9.12 | 6.09 |
| Bud Hair | Glabrous | Glabrous | Glabrous |
| Bud Color | 7.5Y 6/10 | 7.5Y 7/8 | 5Y 7/10 |
| Bud Wax | No | No | No |
| Leaf: | | | |
| Midrib | | | |
| Abaxial Color | 7.5Y 6/10 | 7.5Y 8/10 | 7.5Y 9/2 |

TABLE 1-continued

| Trait | Variety L99-226 | Female HoCP89-846 | Male LCP81-30 |
|---|---|---|---|
| Adaxial Color | 8.5Y 8.5/2 | 7.5Y 8.5/4 | 2.5GY 4/6 |
| Dewlap Shape | Ascending squarish | deltoid | flaring ligulate |
| Dewlap Color | 10Y 4/6 | 10Y 4/6 | 10Y 5/6 |
| Ligule Color | 10YR 3/2 | 10YR 4/2 | 10YR 5/2 |
| Ligule Length (mm) Avg. 10 | 3.97 | 3.69 | 4.83 |
| Ligule Width (mm) Avg. 10 | 19.28 | 18.26 | 21.99 |
| Ligule Hair | Yes | Yes | No |
| Leaf Sheath Hair | Slight | None | Moderate |

Figure 4:
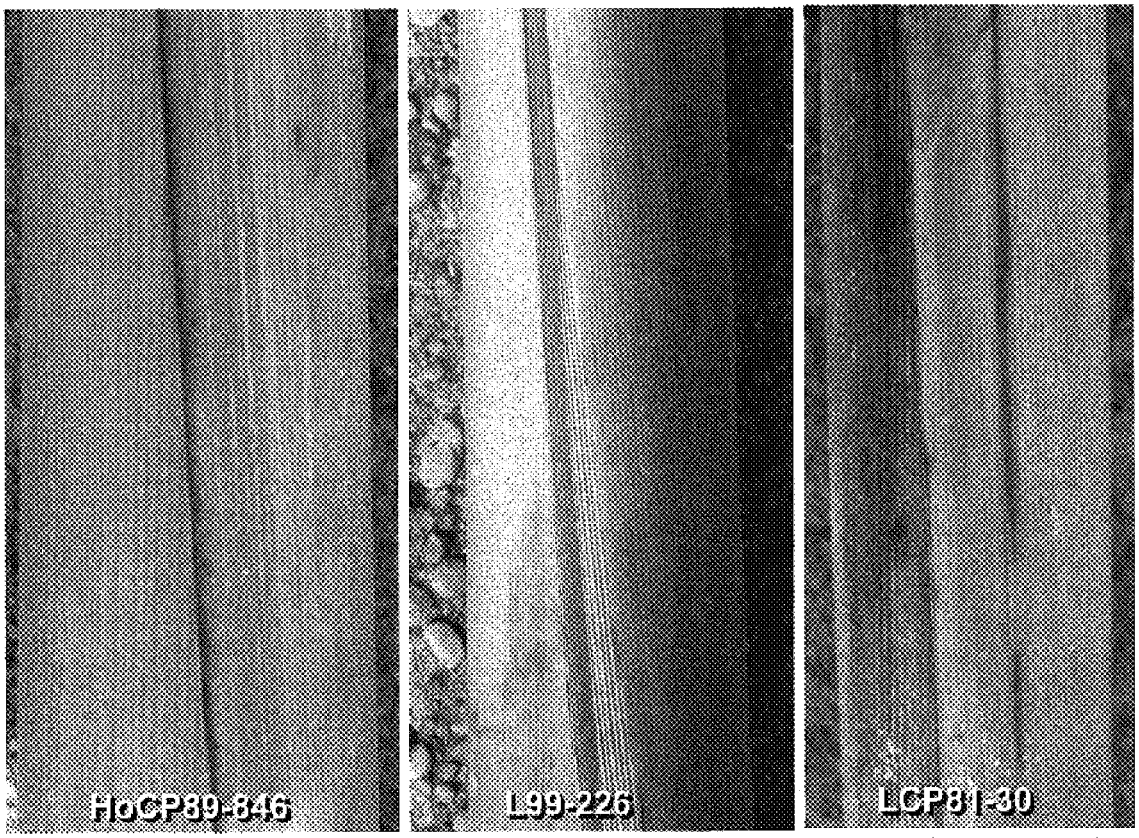
FIG. 4 is a color photograph of the leaf sheath of the novel variety of sugarcane identified as 'L99-226' and other sugarcane varieties identified as 'HoCP89-846' and 'LCP81-30', which were used for comparison tests.

FIG. 4 depicts the leaf sheaths of 'HoCP89-846', 'L99-226', and 'LCP81-30'. On the abaxial side of the leaf sheath, all three varieties exhibited glabrous leaves.

Figure 5:
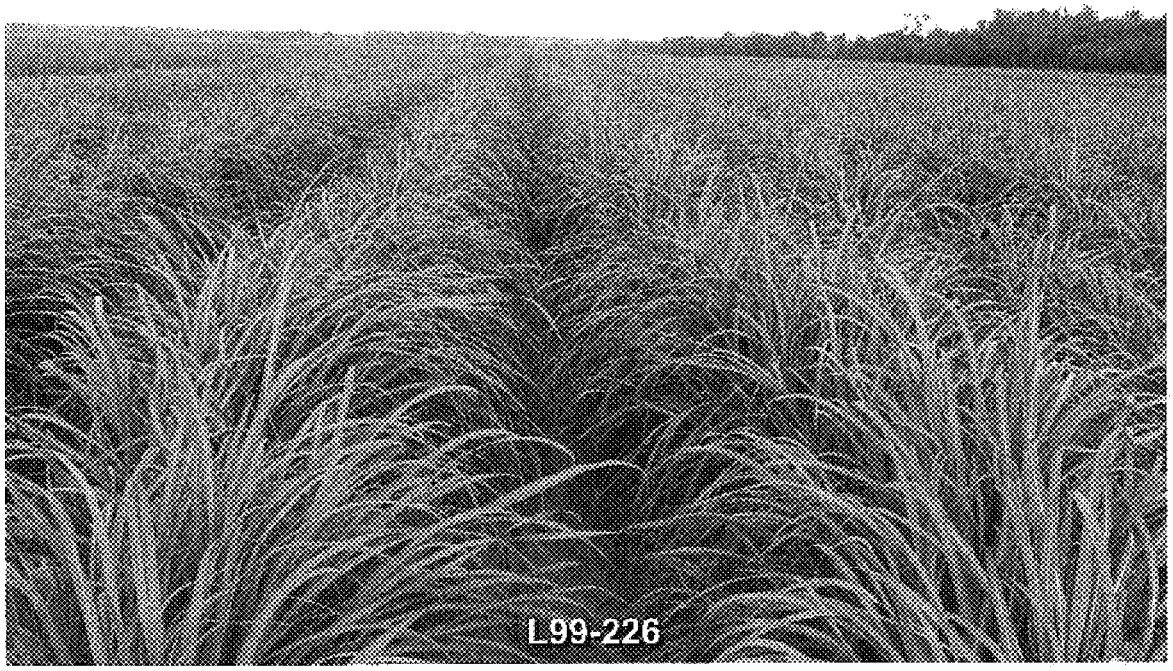
FIG. 5 is a color photograph of a plant cane crop of 'L99-226' in early May, 2006 in Plaquemine, La.

FIG. 5 depicts early spring growth habit of 'L99-226'. The canopy structure of 'L99-226' in early spring was extremely drooping, which erects itself slightly as growth increases. Stalks of 'L99-226' tended to lodge as growth approached late summer and early fall.

Under normal growing conditions in Louisiana, 'L99-226' does not flower. The following flower description was obtained from a 38 L can culture of 'L99-226' grown in St. Gabriel, La., on Sep. 28, 2006 (approximately 130-145 days in age from spring emergence). Each inflorescence (tassel) had a main axis and lateral axes of the first, second, and third order. 'L99-226' exhibited a cylindrical-shaped inflorescence peduncle, degenerating from the base, with a width and length of approximately 6.07 mm and 40-50 mm, respectively. 'L99-226' exhibited pubescence throughout, with short, appressed, silvery pilose hairs [R (red)-Y (yellow) 9/10Y (yellow)]. 'L99-226' had a 590-600 mm long inflorescence main axis with some pilose hairs. Primary branches of 'L99-226' were 300-330 mm long and exhibited appressed racemose branches. Rachis internodes of 'L99-226' were glabrous from the bottom of the main axis, and exhibited a few setaceous hairs towards the apex of the main axis. The apex of 'L99-226' was predominantly grooved. Each spikelet had a single flower comprising three or four glumes, two lodicules, a whorl of three stamens, and a single ovary with two feathery stigmas. Sessile spikelets of 'L99-226' were 3.0-4.5 mm long with white [R (red)-Y (yellow) 9/10Y (yellow)] callus hairs, about 6-10 mm long. The sessile spikelets of 'L99-226' were lanceolate, acuminate, and had membranous glumes, lemma with a hyaline scale, and stamens (3.0-3.5 mm long) comprising purple [2.5 R (Red) 2/6] anthers and white [R (Red)-Y (yellow) 9/10Y (yellow)] filaments. Pedicellate spikelets of 'L99-226' were ovate, acute, rounded at the base, and 5.0-6.0 mm long. Glumes of the pedicillate spikelets of 'L99-226' were membranous; lemmas were hyaline; and stamens were comprised of purple [2.5 R (Red) 2/6] anthers and white [R (red)-Y (yellow) 9/10Y (yellow)] filaments. See G. C. Stevenson. 1965. Flowering in Sugar Cane. pp. 72-97. In: Genetics and Breeding of Sugar Cane. Tropical Science Series. Longmans, Green and Co. Ltd, London.

Example 1

Test Conducted

To confirm that 'L99-226' was a new variety, controlled tests (e.g., pathogen responses and yield), were conducted in St. Gabriel, La. Fifty mechanically harvested, outfield variety trials conducted across south Louisiana involving the replication of 'LCP85-384', 'HoCP91-555', 'HoCP96-540', 'L97-128', and 'L99-233' were selected for comparison tests with 'L99-226' because of their commercial dominance or potential in the Louisiana sugarcane market. The parents of 'L99-226' were not included in the yield trials.

Diseases that commonly affect the growth of sugarcane were selected to test for pathogen responses in all the varieties. The reactions to sugarcane mosaic and sorghum mosaic viruses were as follows: 'L99-226' was moderately resistant, 'HoCP89-846' was resistant, and 'LCP81-30' was susceptible. 'L99-226' and 'LCP81-30' exhibited moderate resistant to smut (caused by *Ustilago scitaminea* Sydow & P. Sydow), whereas 'HoCP89-846' exhibited resistance to smut. 'L99-226' and 'LCP81-30' similarly exhibited moderate resistance to rust (caused by *Puccinia melanocephala* H. and P. Sydow), whereas 'HoCP89-846' exhibited resistance to this disease. 'L99-226' and 'LCP81-30' both exhibited moderate resistance to leaf scald (caused by *Xanthomonas albilineans* Ashby, Dowson) under natural field infection conditions. 'HoCP89-846' was susceptible to leaf scald disease. The effect of yellow leaf disease on the yield of 'L99-226' and its parents are unknown. Similar to both of its parents, 'L99-226' exhibited significant yield loss in ratoon crops from ratoon stunting disease (caused by *Clavibacter xyli* subsp. *xyli* Davis). 'L99-226' was resistant to the sugarcane borer (caused by *Diatraea saccharalis* Fabricius). Resistance of 'HoCP89-846' and 'LCP81-30' to sugarcane borer is unknown. Field observations showed that 'L99-226' was no more susceptible to herbicides commonly used for weed control than other commercially grown sugarcane varieties. Sugarcane disease and sugarcane borer ratings of 'L99-226', 'HoCP89-846' and 'LCP81-30' are shown in Table 2.

No other formal trials have been conducted to date on 'L99-226' for other insect pests. 'L99-226' does not appear to show any novel insect resistance.

TABLE 2

| Variety | Mosaic | Smut | Rust | Leaf Scald | Ratoon Stunting Disease | Sugarcane Borer |
|---|---|---|---|---|---|---|
| 'L99-226' | MR | MR | MR | MR | S | R |
| 'HoCP89-846' | R | R | R | S | S | U |
| 'LCP81-30' | S | MR | MR | MR | S | U |
| 'HoCP91-555' | R | R | MS | MR | S | S |
| 'Ho95-988' | R | MS | MS | MR | MS | S |
| 'HoCP96-540' | R | R | MR | R | MS | S |
| 'L97-128' | R | MS | MR | MR | S | S |

"R"—Resistant; "MR"—Moderately Resistant; "S"—Susceptible, "MS"—Moderately Susceptible; and "U"—Unknown To determine yield, fifty mechanically harvested, outfield variety trials involving the replication of 'LCP85-384', 'HoCP91-555', 'HoCP96-540', 'L97-128', 'L99-226', and 'L99-233' were conducted between the years 2003 and 2005 at various locations within Louisiana. The varieties were planted in Balwin silty clay loam in St. Mary Parish, Commerce silt loam in Pointe Coupee Parish, Commerce silt loam in St. James Parish, Commerce silt loam in Lafourche Parish, Commerce silt loam in Assumption Parish, Jeanerette silt loam in Iberia Parish, Patout silt loam in St. Martin Parish, Commerce silt loam in St. John the Baptist Parish, and Sharkey clay in Terrebonne Parish. Each block/plot was fertilized with nitrogen, potassium, and phosphorous according to standard farm practices associated with each operation. 'L99-226' produced an average fiber content of 12.1% after twenty trials, which was slightly higher than the 11.9% average fiber content produced by 'LCP85-384'. Data for sugar yield, cane yield, sucrose content, stalk weight, and stalk population are shown in Table 3.

TABLE 3

| Variety | Sugar Yield (Mt/ha) | Cane Yield (Mt/ha) | Sucrose Content [%)/Mt] | Stalk Weight (kg) | Stalk Population (stalks/ha) |
|---|---|---|---|---|---|
| | | Plant-cane crop (26)† | | | |
| 'LCP85-384' | 8.20 | 60.3 | 13.6 | 0.85 | 72,581 |
| 'HoCP91-555 | 9.15+ | 65.2+ | 14.0+ | 0.90+ | 74,265 |
| 'HoCP96-540' | 9.92+ | 71.0+ | 14.0+ | 1.09+ | 67,384– |
| 'L97-128' | 9.19+ | 65.9+ | 14.0+ | 1.07+ | 62,091– |
| 'L99-226' | 10.63+ | 71.9+ | 14.8+ | 1.25+ | 59,290– |
| 'L99-233' | 6.69+ | 71.0+ | 13.7 | 0.86 | 85,385+ |
| | | First ratoon crop (17)† | | | |
| 'LCP85-384' | 7.54 | 55.6 | 13.7 | 0.69 | 81,757 |
| 'HoCP91-555 | 8.76+ | 61.2+ | 14.3+ | 0.78+ | 79,124 |
| 'HoCP96-540' | 8.91+ | 63.4+ | 14.1+ | 0.88+ | 73,455– |
| 'L97-128' | 8.50+ | 60.5+ | 14.1+ | 0.89+ | 68,135– |
| 'L99-226' | 9.72+ | 65.2+ | 15.0+ | 1.03+ | 63,929– |
| 'L99-233' | 8.77+ | 63.4+ | 13.9 | 0.72 | 89,582+ |
| | | Second ratoon crop (7)† | | | |
| 'LCP85-384' | 6.80 | 50.0 | 13.6 | 0.63 | 80,258 |
| 'HoCP91-555 | 6.69 | 48.8 | 13.7 | 0.63 | 76,506 |
| 'HoCP96-540' | 7.41 | 54.7 | 13.6 | 0.77+ | 70,877 |
| 'L97-128' | 7.72 | 56.7+ | 13.6 | 0.76+ | 73,633 |
| 'L99-226' | 8.93+ | 58.7+ | 15.1+ | 0.90+ | 65,816– |
| 'L99-233' | 8.33+ | 65.3+ | 13.3 | 0.63 | 98,242+ |

†Number in parentheses represents the total number of trials. Varieties that are significantly higher or lower than 'LCP85-384' are denoted by a plus (+) or minus (–), respectively. The analysis was performed using the SAS (v 9.0) statistical software package (SAS Institute Inc., Cary, North Carolina).

First ratoon maturity tests were conducted in Chacahoula, La. to compare the percentage of sucrose content per ton of cane of 'L99-226', 'LCP85-384', 'HoCP85-845', 'HoCP91-555', 'Ho95-988', 'HoCP96-540', 'L97-128', and 'L99-233' as shown in Table 4. 'L99-226' demonstrated early maturity and continued to accumulate sucrose throughout the harvest, as shown in Table 4. Comparing all varieties across all sampling dates 'L99-226' exhibited a value of 12.5%, second only to L97-128. Its value of 15.7% at the final sampling dates made it one of the higher sucrose content varieties available for commercial production in Louisiana.

TABLE 4

| | 2005 Harvest Dates | | | | | | | Ave. by |
|---|---|---|---|---|---|---|---|---|
| Variety | 9/12 | 9/28 | 10/12 | 10/24 | 11/07 | 11/21 | 12/05 | Variety |
| | % Recovery per Mt | | | | | | | |
| LCP85-384 | 7.8 | 9.5 | 11.0 | 12.6 | 14.0 | 14.7 | 15.2 | 12.1 |
| HoCP85-845 | 9.2 | 10.5 | 11.3 | 13.0 | 13.6 | 13.7 | 14.5 | 12.3 |
| HoCP91-555 | 8.0 | 10.0 | 12.0 | 13.1 | 13.8 | 14.8 | 14.8 | 12.4 |
| Ho95-988 | 7.7 | 9.5 | 10.7 | 12.6 | 13.4 | 13.9 | 15.1 | 11.8 |
| HoCP96-540 | 8.2 | 9.6 | 10.6 | 12.5 | 13.3 | 14.5 | 15.0 | 11.9 |
| L97-128 | 9.7 | 10.8 | 11.8 | 12.8 | 13.9 | 14.5 | 14.6 | 12.6 |
| L99-226 | 8.6 | 9.8 | 10.7 | 13.1 | 14.4 | 15.1 | 15.7 | 12.5 |
| L99-233 | 9.1 | 10.9 | 11.9 | 12.7 | 13.4 | 14.0 | 14.5 | 12.3 |
| Ave. by Date | 8.6 | 10.1 | 11.3 | 12.7 | 13.6 | 14.2 | 14.7 | 12.2 |

We claim:

1. A new and distinct variety of *Saccharum* sp. plant named 'L99-226', as described and illustrated in the specification herein.

* * * * *